(12) United States Patent
Hogen

(10) Patent No.: US 8,028,350 B2
(45) Date of Patent: Oct. 4, 2011

(54) ADJUSTABLE EYECUP EYEWEAR AND METHODS OF USE

(75) Inventor: John E. G. Hogen, Reno, NV (US)

(73) Assignee: Pan-Optx, Inc., Pleasanton, CA (US)

( * ) Notice: Subject to any disclaimer, the term of this patent is extended or adjusted under 35 U.S.C. 154(b) by 422 days.

(21) Appl. No.: 12/319,187

(22) Filed: Dec. 31, 2008

(65) Prior Publication Data

US 2009/0165184 A1 Jul. 2, 2009

Related U.S. Application Data

(60) Provisional application No. 61/018,216, filed on Dec. 31, 2007.

(51) Int. Cl.
*A61F 9/02* (2006.01)

(52) U.S. Cl. .................................. 2/440; 2/448

(58) Field of Classification Search ............. 2/440, 431, 2/449, 13, 439, 442, 448, 454; 351/41, 43, 351/118
See application file for complete search history.

(56) References Cited

U.S. PATENT DOCUMENTS

| | | | |
|---|---|---|---|
| 2,108,074 A | 2/1938 | McMahon | |
| 2,679,191 A * | 5/1954 | Tomlin | 351/59 |
| 2,998,610 A * | 9/1961 | Spero | 2/13 |
| 3,413,057 A * | 11/1968 | Carmichael | 351/47 |
| 3,901,589 A * | 8/1975 | Bienenfeld | 351/47 |
| 4,253,745 A * | 3/1981 | Bizzarri | 351/45 |
| 4,952,043 A * | 8/1990 | Werner et al. | 351/47 |
| 5,129,109 A | 7/1992 | Runckel | |
| 5,170,502 A * | 12/1992 | Hegendorfer et al. | 2/13 |
| 5,335,025 A * | 8/1994 | Wang | 351/47 |
| 5,357,292 A * | 10/1994 | Wiedner | 351/105 |
| 5,422,684 A | 6/1995 | Keller | |
| 6,178,561 B1 * | 1/2001 | Cheng | 2/431 |
| 6,715,873 B2 * | 4/2004 | Nahmias | 351/44 |
| 6,988,798 B1 | 1/2006 | Duffie | |
| 7,013,495 B2 | 3/2006 | Simmons, Sr. | |
| 7,036,927 B2 | 5/2006 | Kopfer | |
| 7,058,991 B2 * | 6/2006 | Hartman et al. | 2/437 |
| 7,083,276 B2 | 8/2006 | Olney | |
| 2004/0051839 A1 | 3/2004 | Tagawa | |

* cited by examiner

*Primary Examiner* — Danny Worrell
(74) *Attorney, Agent, or Firm* — Holland & Hart LLP

(57) ABSTRACT

Described herein are various embodiments of eyewear provided for advantageous use in sports and work, as well as in casual activity. According to one embodiment, an eyeglass can include a frame and an eyecup assembly coupled to the frame. The eyecup assembly can include a resilient side member that has a first proximal portion that is fixed relative to the frame and a second distal portion that is movable relative to the frame and biased toward the frame. The eyecup assembly can also include an adjustment mechanism that is coupled to the resilient side member and positioned at least partially between the resilient side member and the frame. The adjustment mechanism can be selectively operable to flex the resilient side member to move the second distal portion away from the frame and to un-flex the resilient side member to move the second distal portion toward the frame.

22 Claims, 5 Drawing Sheets

ADJUSTABLE EYECUP EYEWEAR AND METHODS OF USE

REFERENCE TO PENDING PRIOR PATENT APPLICATION

This application claims the benefit under 35 U.S.C. 119 (e) of U.S. Provisional Patent Application No. 61/018,216, filed Dec. 31, 2007 by Jackson Hogen for "ADJUSTABLE EYE-CUP EYEWEAR AND METHODS OF USE," which patent application is hereby incorporated herein by reference.

FIELD

This disclosure pertains to eyewear. More particularly, this disclosure pertains to eyewear, including glasses and sunglasses, having an adjustable eyecup.

BACKGROUND

Wearing of eyeglasses and the like while engaged in vigorous activity can be difficult for various reasons. One key reason is a fundamental inability of most eyeglass frames to provide a protective seal around a wearer's eyes for preventing wind, dust, dirt, moisture, glare, ultraviolet radiation, and other contaminants and debris from contacting, and potentially damaging, the wearer's eyes.

Many people wear eyeglasses for reasons other than, or in addition to, vision correction. Well-known examples are the large number of different types of "sunglasses" that reduce the intensity (and/or change the wavelength) of light reaching the wearer's eyes. Other well-known examples are so-called "safety glasses" usually used for eye protection in industrial and laboratory environments. Yet other well-known examples are various "goggles" and the like.

As used herein, "eyewear" generally encompasses all of various eyeglass types summarized above as well as any other analogous device configured to fit to a person's face and that includes a "frame" and "lenses." The frame typically has a front portion situated largely in front of the wearer's eyes. The lenses are mounted to the front portion and transmit at least some light to the wearer's eyes. Mounted to the front portion are "temple pieces" that extend rearward from the front portion to engage and/or rest upon the wearer's ears. The temple pieces usually, but not necessarily, are hinged to the front portion.

To address the concerns raised by the need for protection of the wearer's eyes during activity, various schemes have been adopted. For example, certain types of eyewear, notably safety goggles and certain types of eyeglasses, employ shields, liners, and other sealing members for protecting a wearer's eyes during use, such as described in U.S. Pat. Nos. 7,083,276; 7,036,927; 6,988,798; and 7,013,495, as well as U.S. Patent Publication No. 2004/0051839. Unfortunately, the sealing members of these types of eyewear are not adjustable to conform to various face sizes and shapes. Therefore, such eyewear may fail to provide adequate protection for the wearer's eyes during activity, provide sufficient venting, or retain the versatility from which, for example, extended wear may benefit.

Some schemes have been tried to improve the protection of a wearer's eyes by providing adjustable sealing members. For example, a first scheme involves adjusting the spacing between two lenses or pivoting eye cups to conform to the facial contour of a wearer, such as discussed in U.S. Pat. No. 2,108,074. A second scheme involves inflating or deflating an inflatable cushion member to provide an adjustable seal against contaminants, such as discussed in U.S. Pat. No. 5,129,109. A third scheme involves retracting or extending, such as by pivoting, retractable eyeshields to provide eye protection that can be adjusted to an individual wearer, such as discussed in U.S. Pat. No. 5,422,684. Unfortunately, these various schemes tend to be highly specialized and do not address all needs, especially needs posed by concepts of style and utility that arise with modern sports eyeglasses.

SUMMARY

Described herein are various embodiments of eyewear provided for advantageous use in sports and work, as well as in casual activity. The eyewear can have one or more adjustable eyecups for providing a custom fit around the eyes and protecting the eyes from undesirable contaminants. More specifically, in some embodiments, the eyewear can include flexible eyecups that are adjustable by actuation of an adjustment mechanism, such as a cam assembly or detent mechanism.

According to one embodiment, an eyeglass can include a frame and an eyecup assembly coupled to the frame. The eyecup assembly can include a resilient side member that has a first proximal portion that is fixed relative to the frame and a second distal portion that is movable relative to the frame and biased toward the frame. The eyecup assembly can also include an adjustment mechanism that is coupled to the resilient side member and positioned at least partially between the resilient side member and the frame. The adjustment mechanism can be selectively operable to flex the resilient side member to move the second distal portion away from the frame and to un-flex the resilient side member to move the second distal portion toward the frame.

In some implementations, the adjustment mechanism includes a detent mechanism operable to flex and un-flex the resilient side member. The detent mechanism can include a positioner portion that has a plurality of apertures and a catching portion that is movable relative to the positioner portion and has a resiliently biased catch engageable with the apertures.

In some implementations, the adjustment mechanism can include a cam that is movably, e.g., rotatably, engageable with a cam guide. The cam can be movable, e.g., rotatable, relative to the cam guide to flex and un-flex the resilient side member.

In some implementations, the eyecup assembly can include a rigid side member that is mounted to the frame. The first proximal portion of the resilient side member can be fixed to the rigid side member and the second distal portion of the resilient side member can be movable relative to the rigid side member. In specific implementations, the resilient side member can be sealingly engageable with the rigid side member as the second distal portion moves away from and toward the frame. In yet other specific implementations, the second distal portion can be movable into one of a plurality of predetermined positions relative to the frame.

In some implementations, the eyecup assembly can be a modular self-contained unit.

In some implementations, the eyecup assembly can extend continuously about an entire periphery of the frame.

In some embodiments, the flexible or moveable portion of an eyecup, or portion thereof, can be retracted or be adjusted into the frame.

According to another embodiment, an eyecup assembly for use with an eyeglass having a frame can include a body that includes at least one side portion. The body can be attachable to a frame of an eyeglass such that the at least one side portion at least partially overlays an eye of a wearer when the eyeglass is worn by the wearer. The eyecup assembly can also include at least one side member that is coupled to the body and partially overlay the at least one side portion. The at least one side member can be movable relative to the at least one side portion. Further, the eyecup assembly can include at least one adjustment mechanism that is positioned at least partially between a respective at least one side member and a respective at least one side portion of the body. The at least one adjustment mechanism can include a first portion coupled to a respective one of the at least one side portion and at least one side member and a second portion coupled to the other of the at least one side portion and at least one side member. The first and second portions of the adjustment mechanism are adjustably engageable with each other to move the at least one side member into one of a plurality of predetermined positions relative to the at least one side portion.

In some implementations, the at least one adjustment mechanism includes a detent mechanism. Further, first portion can be a positioner portion having a plurality of apertures and the second portion can be a catching portion that is movable relative to the positioner portion. The catching portion can also have a resiliently biased catch that is engageable with the apertures of the positioner portion.

In some implementations, the at least one adjustment mechanism can include a cam assembly that has a cam that is movable relative to a cam guide to move the at least one side member relative to the at least one side portion. In certain implementations, the cam guide of the eyecup assembly includes a plurality of stepped portions that each correspond to one of the plurality of predetermined positions. The cam guide can include an engager separately engageable with each of the stepped portions to place the at least one side member into a respective one of the plurality of predetermined positions. In one specific implementation, the engager can be a generally tooth-shaped projection having sloped edges, the cam guide can include a plurality of sloped transition portions each joining adjacent stepped portions of the plurality of stepped portions, and the sloped transition portions and the sloped edges can interact to facilitate movement of the engager between the plurality of stepped portions.

In some implementations, the at least one side member can be sealingly engageable with the at least one side portion. In a specific implementation, the at least one side portion can include a projection extending adjacent a periphery of the side portion, the at least one side member can include a channel extending adjacent a periphery of the side member, and the projection can be at least partially positionable within the channel to form a seal between the side portion and the side member when the side member is in any of the plurality of predetermined positions.

In some implementations, the plurality of predetermined positions can include a first position in which the at least one side member is adjacent the at least one side portion, a second position in which the at least one side member is distanced away from the at least one side portion a first distance, and a third position in which the at least one side member is distanced away from the at least one side portion a second distance.

In some implementations, the cam guide can be integral with the at least one side portion. The eyecup assembly can also include a flexible eye protector that is positioned intermediate the at least one side portion and at least one side member. The at least one side member can be sealingly engageable with the at least one side portion via the flexible eye protector.

In some implementations, the at least one side member can be made of a resiliently flexible material. In these implementations, as the at least one side member moves from one predetermined position to another predetermined position, a first portion of the at least one side member remains fixed relative to the at least one side portion and a second portion of the at least one side member is flexed about the first portion. In a specific implementation, the at least one side member can have a bias toward the at least one side portion. In this implementation, the cam can be maintained in engagement with the cam guide by the bias of the at least one side member.

In yet some implementations, the body can include a respective side portion for each eye of the wearer. The at least one side member can include a respective side member for each eye of the wearer. The at least one adjustment mechanism can include a respective adjustment mechanism for each eye of the wearer.

According to another embodiment, a method for adjusting fit of an eyewear to a wearer can include providing an eyewear that includes a lens portion or shield and an eyecup assembly coupled to the lens portion. The eyecup assembly can include (i) at least one fixed side member that is fixed relative to the lens portion; (ii) at least one resiliently flexible side member that is movably coupled to the at least one fixed side member; and (iii) at least one adjustment mechanism that is coupled to the at least one fixed side member and at least one resilient side member. The method can further include adjusting the adjustment mechanism to flex the at least one resiliently flexible side member away from the at least one fixed side member or un-flex the at least one resiliently flexible side member toward the at least one fixed side member.

In some implementations, the at least one adjustment mechanism comprises a detent mechanism that has a positioning portion having a plurality of recesses coupled to a respective one of the at least one fixed side member and at least one resiliently flexible side member and a catching portion that has a catch engageable with the recesses and coupled to the other of the at least one fixed side member and at least one resiliently flexible side member. Further, adjusting the adjustment mechanism can include urging the catch into and out of engagement with the recesses.

In specific implementations, the at least one resiliently flexible side member is movable into a plurality of positions relative to the at least one fixed side member. Further, the catch can be biased in a recess engaging position. In these implementations, adjusting the adjustment mechanism can include applying a pressure to the catch sufficient to overcome the bias and move the catch out of the recess engaging position.

In some implementations, the adjustment mechanism can include a cam rotatably engageable with a cam guide. In these implementations, adjusting the cam mechanism can include rotating the cam relative to the cam guide. In certain implementations, the cam guide can include a plurality of stepped portions each corresponding to one of a plurality of predetermined positions. The cam guide can include an engager separately engageable with each of the stepped portions. Also, in such certain implementations, adjusting the adjustment mechanism can include engaging a stepped portion of the plurality of stepped portions that corresponds with a desired predetermined position with the engager to place the at least a portion of the at least one resilient side member in the desired predetermined position.

In some implementations, adjusting the adjustment mechanism can include adjusting the adjustment mechanism to bend at least a portion of the at least one resilient side member.

In some implements, certain embodiments can aid in preventing or treating dry eye, dysfunctional tear syndrome, ocular surface disease, or other possible problems or disorders of the eye.

It is to be understood that the foregoing is a summary of certain aspects or features of embodiments disclosed herein. Embodiments of the invention need not necessarily include all such aspects or features or address issues noted in the Background. The foregoing and other features and advantages will become more apparent from the following detailed description, which proceeds with reference to the accompanying figures.

BRIEF DESCRIPTION OF THE DRAWINGS

The preferred and other embodiments are shown in the accompanying drawings wherein.

DETAILED DESCRIPTION

This disclosure is set forth in the context of representative embodiments that are not intended to be limiting in any way.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Figure 1:
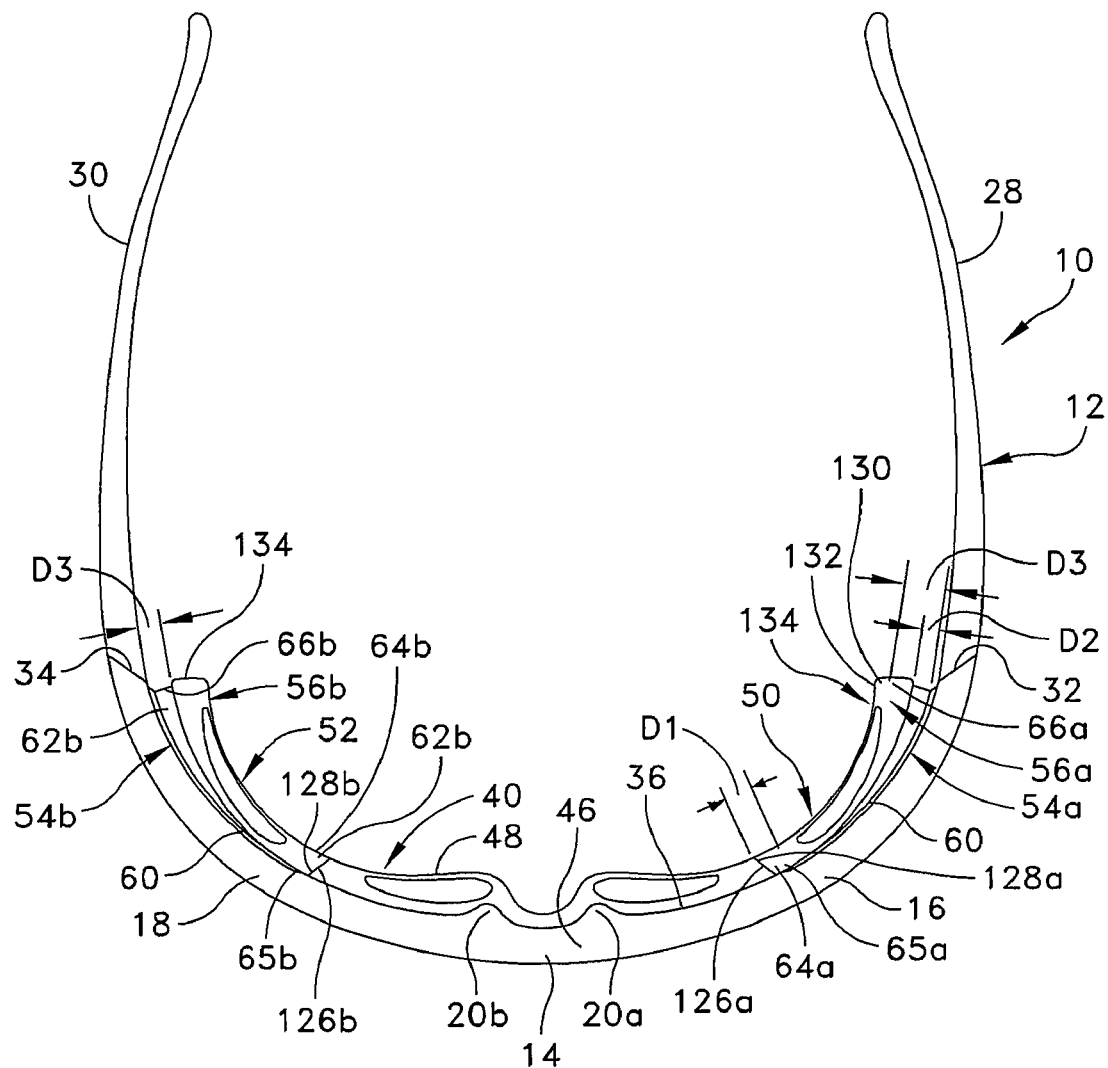
FIG. 1 is a top plan view of an eyeglass having an eyecup according to one exemplary embodiment.

A representative embodiment of an eyeglass is depicted in FIG. 1. The eyeglass 10 comprises a substantially rigid frame 12. The frame 12 is configured to be situated, when fitted to a wearer's face, at least in front of the wearer's face at about eye level. The frame 12 defines a bridge 14 that connects together a left lens mounting 16 and a right lens mounting 18. The frame 12 also comprises left and right nose-pad regions 20a, 20b, respectively. Each lens mounting 16, 18 accommodates a respective lens portion (not shown) (each portion generally being a respective "lens" because it is intended to pass light to a respective eye). In some embodiments, the lens portions include an integral connecting portion that extends along the bridge 14. Hence, the lens portions can be an integral unit. However, in alternative configurations, the lens portions can be individual respective units.

In the depicted embodiment, the frame 12 (principally the lens mountings 16, 18 thereof, beginning at the bridge 14) curves rearwardly in a manner that follows the curve of the wearer's face, but without actually contacting the wearer's face. This rearward curve is called "wrap." Attached to the frame are a left temple piece 28 and a right temple piece 30. In the illustrated embodiment, the temple pieces 28, 30 are pivotally mounted to respective lateral edges 32, 34 of the frame 12 via a hinge mechanism (not shown).

The eyeglass 10 also comprises an eyecup, or eye sealing member, 40 extending about a periphery of the frame 12 and positioned between the frame and a wearer's eyes when the eyeglass is worn by the wearer. The eyecup 40 includes an upper central portion 42 proximate an upper edge 46 of the bridge 14 and a lower central portion 44 proximate the nose-pad regions 20a, 20b. The eyecup 40 further includes left and right side assemblies 50, 52 respectively, extending about the left and right lens mountings 16, 18, respectively. The eyecup 40 defines an aperture 38 having a size and shape corresponding generally to the size and shape of the lens portions of the eyeglass 10 such that, when the eyecup 40 is coupled to the frame 12, the wearer can see through the lens portion via the aperture 38. As shown, the aperture 38 is a single aperture. However, in some embodiments, such as embodiments having separate lens portions, the aperture 38 can comprise two apertures each corresponding to respective lens portions.

The eyecup 40 is coupled to an inner surface 36 of the frame 12 and extends generally transversely away from the frame 12 toward the wearer's face. When worn, the eyecup 40 is configured to contact respective portions of the wearer's face about the eyes to create a seal between the eyecup and the wearer's face against contaminants that may be harmful to the eyes. For example, the upper central portion 42 is configured to contact and form a seal between the eyecup and a wearer's glabella, i.e., the smooth area between the eyebrows just above the nose; the lower central portion 44 is configured to contact and form a seal between the eyecup and a wearer's nose; and the left and right side assemblies 50, 52 overlay, e.g., are adjacent to, respective left and right eyes of the wearer, and are configured to contact and form a seal between the eyecup and the wearer's left and right eye sockets, respectively. In other words, in some embodiments, the eyecup 40 forms a continuous seal about the wearer's eyes.

The eyecup 40 can be permanently, semi-permanently, or removably coupled to the inner surface 36 of the frame 12 in any of a number of ways. For example, in some embodiments, the eyecup 40 is bonded to the inner surface 36 through use of an adhesive, or other bonding technique. In other embodiments, the eyecup 40 is fastened to the inner surface 36 through use of a fastener assembly such as is commonly known in the art. In yet other embodiments, the eyecup 40 can be formed integrally with the frame to form a one-piece construction with the frame.

The eyecup left and right side assemblies 50, 52 are independently adjustable to provide a customizable fit and potentially, a more effective seal, for a wearer of the eyeglass. The side assemblies 50, 52 includes respective left and right fixed portions 54a, 54b and respective left and right movable portions 56a, 56b. The fixed portions 54a, 54b are fixed relative to the upper and lower central portions 42, 44, and thus the frame 12 and the wearer's face. Conversely, the movable portions 56a, 56b are movable relative to the upper and lower central portions 42, 44, and thus the frame 12 and the wearer's face.

Figure 2:
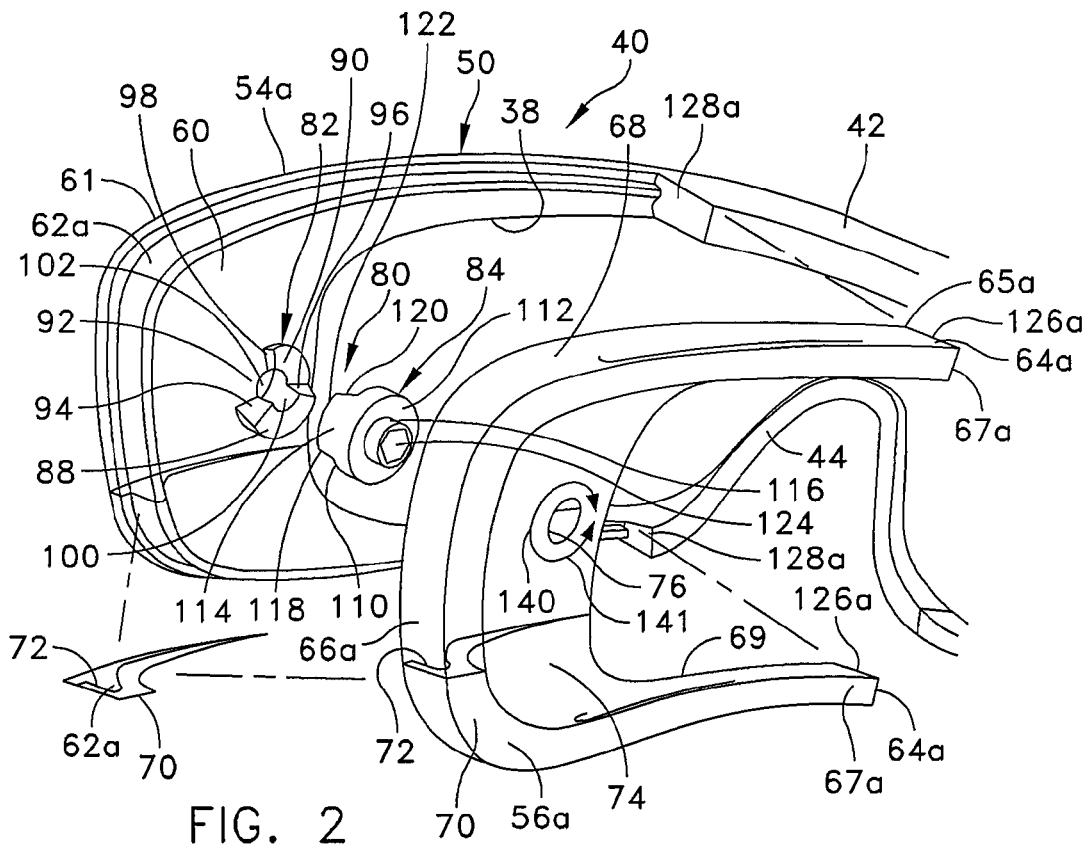
FIG. 2 is an exploded partial perspective view of the eyecup shown in FIG. 1.

The fixed portions 54a, 54b each include a base wall 60 (see FIGS. 1 and 2). The fixed portions 54a, 54b also include a respective ridge 62a, 62b extending about and generally transversely from the base wall 60 adjacent an outer periphery 61 of the base wall. In the illustrated embodiment, the fixed portions 54a, 54b are integrally formed with the upper and lower central portions 42, 44 to form a one-piece eyecup body 48.

In alternative embodiments, the fixed portions 54a, 54b can each comprise a separate unit attached or mounted to the upper and lower central portions 42, 44 to form the eyecup body 48.

In certain embodiments, the eyecup 40 includes two separate body portions that are individually attached to the eyeglass frame 12. Each body portion can include a respective side assembly 50, 52 and may or may not include a portion of the upper and central portions 42, 44. For example, the upper and lower central portions can be integrated or separately attached to the eyeglass frame 12, or alternatively, the eyeglass 10 does not include upper and lower central portions.

In some embodiments, the eyecup 40 is a self-contained and modular unit. In other words, the eyecup 40 functions independently of the frame 12 such that the eyecup 40 can be attached to and removed from the frame without inhibiting the functionality of or damaging the eyecup or frame. In this manner, the eyecup 40 can be, in certain implementations, interchangeable with two or more frames.

The movable portions 56a, 56b extend from respective proximal end portions 64a, 64b to respective distal end portions 66a, 66b. Referring to FIG. 2, which shows further detail of the left fixed and movable portions 54a, 56a, from which details of the right fixed and movable portions 54b, 56b also will be understood, the left movable portion has an outer periphery 68 that corresponds generally to the outer periphery 61 of the left fixed portion and an inner periphery 69 that corresponds generally to the aperture 38. The left movable portion 56a includes an outer edge portion 70 extending from an upper of the proximal end portions 64a, about the outer periphery 68, to a lower of the proximal end portions 64a. The outer edge portion 70 defines a recess 72 configured to receive at least a portion of the ridge 62a. In the illustrated embodiment, the recess 72 and the ridge 62a are shaped and sized to nestably engage each other when the movable portion 56a is in a first, or fully-retracted, position as explained in more detail below. The movable portion 56a further includes a wall 74 extending between the outer edge portion and the inner periphery 69. The wall 74 defines an aperture 76 for receiving a portion of an adjustment mechanism, which will be explained in more detail below.

The proximal end portions 64a, 64b of the respective movable portions 56a, 56b are coupled to the eyecup body 48 such that the proximal end portions are closer to the upper and lower central portions 42, 44 than the distal end portions 66a, 66b. At least part of the proximal end portions 64a, 64b, such as respective attachment surfaces 65a, 65b, can be coupled to the body 48. The attachment surfaces 65a, 65b are outwardly facing surfaces of the proximal end portions 64a, 64b extending from a proximal end 67a, 67b of the movable portions 56a, 56b a distance D1 (see FIGS. 1 and 2). The proximal end portions 64a, 64b can be coupled to the eyecup body 48 by any of various coupling or bonding techniques. For example, the proximal end portion 64a can be bonded to the eyecup body 48 by placing a bonding material, such as glue, between the attachment surface 65a and the central portions 42, 44 and/or between the attachment surface and the base wall 60. Desirably, the proximal end portions 64a, 64b are fixed relative to the central portions 42, 44, and thus the eyecup body 48 or the frame 12. However, in some embodiments, the proximal end portions 64a, 64b can be allowed to move, such as rotate or pivot, relative to the central portions 42, 44.

In the illustrated embodiment, the movable portions 56a, 56b are made of a resilient and at least partially flexible material having a bias in an un-flexed state. Referring to FIG. 1, when the proximal end portion 64a is coupled to the eyecup body 48 and the movable portion 56a is in an un-flexed state, the movable portion 56a is in a first, or closed, position 130. Accordingly, the movable portions 56a, 56b are biased in the closed position 130. In the closed position 130, the recess 72 is fully nested within the ridge 62a (see detailed portion of FIG. 2), and substantially the entire outer edge portion 70 is in contact with, or at least in very close proximity to, the base wall 60 (see FIG. 1).

The flexibility of the movable portions 56a, 56b allows the distal end portions 66a, 66b to be pivoted, bent, or flexed about the proximal end portions 64a, 64b away from and towards the respective fixed portions 54a, 54b. In other words, when the eyeglass 10 is worn by a wearer, the distal end portions 66a, 66b are movable towards and away from the wearer's face by flexing and un-flexing the movable portions 56a, 56b. In implementations using a bonding material to bond the movable portions 56a, 56b to the central portions 42, 44, the bonding material provides sufficient adhesion between the proximal end portions 64a, 64b and the central portions 42, 44 to maintain the ends in coupling engagement with the central portions as the movable portions 56a, 56b are moved between a flexed and un-flexed state.

Each side assembly 50, 52 includes an adjustment mechanism, such as cam assembly 80 shown in FIG. 2, for adjustably positioning the movable portions 56a, 56b relative to the respective fixed portions 54a, 54b. The details of the cam assembly 80 of the left side assembly 50 can be understood to apply to the cam assembly of the right side assembly 52. The cam assembly 80 is positioned at least partially between the fixed portion 54a and the movable portion 56a. The cam assembly 80 includes a cam guide 82 and a cam 84 that is engageable with and movable, e.g., rotatable, slidable, pivotable, etc., relative to the cam guide 82.

Figure 3:
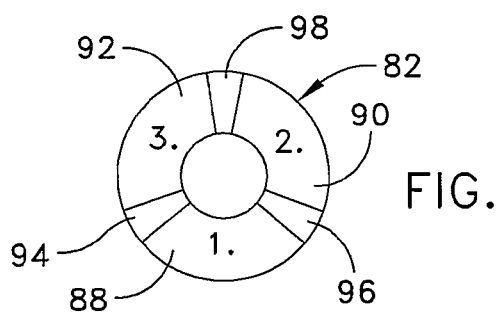
FIG. 3 is a top plan view of a cam guide as shown in FIG. 2.
Figure 4:
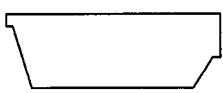
FIG. 4 is a side view of the cam of FIG. 2.
Figure 5:
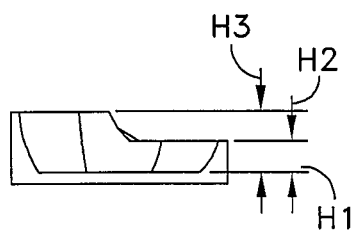
FIG. 5 is this a side view of the cam guide of FIG. 2.

Referring to FIGS. 2 and 3, in the illustrated embodiment, the cam guide 82 has a generally circular outer periphery and is formed integrally with the base wall 60 of the left fixed portion 54a. However, in other embodiments, the cam guide 82 is formed as a separate unit and attached to the base wall 60, such as with fasteners or a bonding adhesive. The cam guide 82 comprises a first stepped portion 88 and a second stepped portion 90 projecting rearwardly generally transversely from the base wall 60. The cam guide 82 further comprises a third stepped portion 92. As shown in FIG. 2, the third stepped portion 92 is a rearward surface of the base wall 60 between the first and second stepped portions 88, 90. Although in the illustrated embodiment, the third stepped portion 92 is essentially a portion of the base wall 60, in other embodiments, the third stepped portion 92 can project rearwardly generally transversely from the base wall 60 in the same manner as the first and second stepped portions 88, 90. The first, second, and third stepped portions 88, 90, 92 have upper surfaces at different heights relative to the base wall 60. For example, in one implementation, the first stepped portion 88 has a height H1, the second stepped portion 90 has a height H2, and the third stepped portion 92 has a height H3 (see FIG. 5). In specific implementations, the height H1 is zero, the height H2 is 2 mm and the height H3 is 4 mm. The first, second, and third stepped portions 88, 90, 92 are adjoined by respective transition portions 94, 96, 98 having sloped surfaces relative to the stepped portions. The cam guide 82 further includes an aperture cut-out 100 defined between the stepped and transition portions. The aperture cut-out 100 is coextensive with an aperture 102 formed in the base wall 60.

The cam 84 extends longitudinally from a first end 110 to a second end 112 with a cam guide engager 114 extending from the first end 110 and an adjustment-tool-receiving-portion 116 extending from the second end 112. The cam-guide engager 114 can be a tooth-shaped projection configured to be separately engageable with the first, second, and third stepped portions 88, 90, 92. The cam-guide engager 114 includes a first angled, or sloped, edge 118 and a second angled, or sloped, edge 120 generally opposite the first angled edge. A guide-contact edge 122 extends between the first and second sloped edges 118, 120. The adjustment-tool-receiving portion 116 defines an aperture 124 configured to receive an adjustment tool (not shown), such as an Allen wrench or key. In other words, the aperture 124 can have the same general cross-sectional shape as the adjustment tool, such as, for example, a hexagonal cross-sectional shape.

The cam 84 is held in engagement with the cam guide 82 between the movable portion 56a and the fixed portion 54a due to the bias of the movable portion 56a. Such a configuration provides certain advantages, such as, for example, the overall number of components required to manufacture the eyecup 40 can be reduced, which can lead to lower costs, increased reliability, and ease in manufacturing.

The adjustment-tool-receiving portion 116 extends at least partially through and is rotatable within the aperture 76. The aperture 76 acts to maintain the cam 84 in proper alignment with the cam guide 82 as the cam rotates relative to the cam guide. When in proper alignment, the aperture 76, aperture 124, and aperture 102 are generally coaxial with each other. The movable portion 56a applies a pressure on the cam 84 such that the cam-guide engager 114 remains in contact with the cam guide 82. More specifically, the guide-contact edge 122 of the cam 84 is maintained in contact with one of the stepped portions 88, 90, 92 of the cam guide 82 due to the bias of the movable portion 56a.

Although in the illustrated embodiments, the cam guide 82 is secured to the fixed portion 54a and the cam 84 is positioned between the cam guide and the movable portion 56a, in other embodiments, the cam guide 82 can be secured, e.g., integrally or attached, to the movable portion and the cam can be positioned between the cam guide and the fixed portion.

The cam assembly 80 is adjustable to position the movable portions 56a, 56b into two or more positions relative to the fixed portions 54a, 54b. For example, referring to FIG. 1, in some embodiments, the movable portions 56a, 56b are adjustable into one of three positions, e.g., the first, or closed, position 130, a second, or intermediate, position 132, and a third, or fully-open, position 134. As described above, in the first position 130, the distal end portions 66a, 66b are in contact with, or at least in very close proximity to, the base wall 60. In the second position 132, the movable portions 56a, 56b are flexed such that the distal end portions 66a, 66b are displaced, or distanced away from the base wall 60, a distance D2. In the third position 134, the movable portions 56a, 56b are flexed such that the distal end portions 66a, 66b are displaced a distance D3. In one specific exemplary implementation, the distance D2 is 2 mm and the distance D3 is 4 mm such that the total adjustability of both the left and right side assemblies 50, 52 is 8 mm. In other implementations, the distances D2 and D3 can be any of various equal or unequal distances.

Referring to FIG. 2, the guide contact edge 122 of the cam-guide engager 114 contacts one of the stepped portions 88, 90, 92 to place the movable portion 56a in the first, second, and third positions 130, 132, 134, respectively. The cam 84 is movable, e.g., rotatable, relative to the cam guide 82 to move the guide-contact edge 122 out of contact with one stepped portion and into contact with another stepped portion to move the movable portion 56a from one position to another position. For example, the cam 84 can be rotated in a first direction, e.g., a clockwise direction 140, to move the guide contact edge 122 from being in contact with stepped portion 88 to being in contact with either stepped portion 90 or stepped portion 92 to move the movable portion 56a from the first position 130 to either the second or third positions 132, 134, respectively.

Rotation of the cam guide engager 114 from one stepped portion to another can be facilitated by the first through third transition portions 94, 96, 98 between the stepped portions and the sloped edges 118, 120 of the cam guide engager 114. For example, from the first position 130, as the cam 84 is rotated in the clockwise direction 140, the sloped edge 120 of the cam guide engager 114 contacts and slides upwardly along the third transition portion 98 of the cam guide 82 until the guide-contact edge 122 contacts the second stepped portion 90 to place the movable portion 56a in the second position 132. Likewise, from the second position 132, as the cam 84 is rotated in the clockwise direction 140, the sloped edge 120 contacts and slides upwardly along the second transition portion 96 until the guide-contact edge 122 contacts the third stepped portion 92 to place the movable portion 56a in the third position 134. From the third position 134, as the cam 84 is rotated in the clockwise direction, the sloped edge 118 contacts and slides downwardly along the first transition portion 94 until the guide-contact edge 122 contacts the first stepped portion 88 to place the movable portion 56a back in the first position 130. Of course, the cam 84 can be rotated in a counterclockwise direction 141 such that the sloped edge 118 slides upwardly along the first and second transition portions 94, 96, respectively, and downwardly along the third transition portion 98 to move the movable portion 56a between the first, second, and third positions 130, 132, 134.

Rotation of the cam 84 with respect to the cam guide 82 can be facilitated by an adjustment tool (not shown). In one implementation, the adjustment tool can be inserted through the aperture 102 in the base wall, along the cut-out 100 in the cam guide 82, through the aperture 124, and matingly engage the walls defining the aperture 124. Rotation of the adjustment tool correspondingly rotates the cam 84. In this implementation, the frame has an aperture (not shown) aligned with the aperture 102 such that the adjustment tool can be inserted through the aperture 102 from a front of the eyeglass 10. In this manner, a wearer can adjust the movable portions 56a, 56b while wearing eyeglass 10. Alternatively, in another implementation, the adjustment tool can be inserted into the aperture 124 in the cam 84 via the aperture 76 of the movable portion 56a from a rear of the eyeglass 10. In such an implementation, the wearer preferably would first remove the eyeglass 10 before adjusting the movable portions 56a, 56b. Therefore, according to some embodiments, the movable portions 56a, 56b can be adjustable via a front or rear of the eyeglass 10.

Although the illustrated embodiments describe movable portions 56a, 56b that are adjustable into one of three positions, in other embodiments, the movable portions 56a, 56b can be adjustable into fewer or more than three positions. For example, the cam guide 82 can have any number of stepped portions corresponding to any number of movable portion positions to provide increased adjustability and customization of the eyecup side assemblies 50, 52 of the eyeglass 10. Of course, the number of positions that can be accommodated is limited in a practical sense by the size of the cam guide 82 and cam 84.

Additionally, although in the illustrated embodiments, each side assembly 50, 52 includes a single cam assembly 80, in other embodiments, each side assembly can include more than one cam assembly to provide even more customization and adjustability of the fit of the eyeglass 10. For example, in certain implementations, one or both of the side assemblies 50, 52 can include two cam assemblies 80. One cam assembly 80 can be positioned proximate a top of the side assembly and the other cam assembly can be positioned proximate a bottom of the side assembly. If desired, the top and bottom cam assemblies can be adjusted equally such that the both a top and bottom portion of the respective movable portion can be positioned an equal distance away from the respective fixed portion. Alternatively, based on a wearer's preference or the particular features of a wearer's face, the top or bottom assembly can be adjusted differently such that either the top portion is at a greater or lesser distance away from the respective fixed portion than the bottom portion and vice versa.

In the illustrated embodiment, in any of the three positions of the movable portions 56a, 56b, the ridge 62a sealingly engages the recess 72 to provide a seal between the movable portion 56a and the fixed portion 48 that restricts contaminants from entering the eye. As used herein, a seal or sealing engagement between two objects is used to define the interaction between the two objects that prevents, restricts, resists or hinders foreign contaminants from passing between the objects. A seal as used herein can be, but is not necessarily, a hermetic seal. In other words, a seal can be an at least partially permeable seal as long as it provides at least some restriction to foreign contaminants.

For example, when the movable portions 56a, 56b are in the first position 130, the recesses 72 and the ridges 62a, 62b are nestably engaged, as shown in FIG. 2, to seal the junction between the movable portions 56a, 56b and the fixed portions 54a, 54b. In the second position 132, the ridges 62a, 62b remains at least partially within, e.g., engaged with, the recesses 72 to maintain the seal between the movable portions 56a, 56b and the fixed portions 54a, 54b. Further, as shown in FIG. 1 in relation to the movable portion 56b and fixed portion 54b, in the third position 134, the ridge 62b remains at least partially within the recess 72 to maintain the seal.

In certain embodiments, a space is defined between the recesses and ridges in each of the three positions to facilitate venting. More specifically, the recesses and ridges can be sealingly engaged to restrict contaminants from entering, and at the same time, allow air to vent through the spaces between the recesses and ridges. Proper venting is important to prevent moisture build-upon the interior of the lens, which can impede vision.

According to one embodiment, in use, a wearer can place the eyeglass 10 on his face and determine if the movable portions 56a, 56b are in contact with, e.g., pressed against, the wearer's face proximate his left and right eye sockets, respectively, and if such contact is comfortable. If so, the eyecup 40 is properly adjusted to resist contaminants from entering the eye in a manner that comfortable to the wearer. If one or both of the movable portions 56a, 56b are pressed too tightly against the wearer's face or if the movable portions are not properly in contact with the wearer's face, the wearer can insert an adjustment tool into the aperture 124 associated with improperly fitting movable portion via either the front of the eyeglass 10 (e.g., while wearing the eyeglass) or the back of the eyeglass (e.g., after removing the eyeglass) and adjust the position of the movable portions to provide a looser or tighter fit. For example, if the movable portion 56a is too tight against the wearer's face, the adjustment tool can be rotated to rotate the cam 84 relative to the cam guide 82 and move the distal end portion 66a from the first position 130 to either the second or third positions 132, 134, or from the second position 132 to the third position 134, to loosen the fit with the wearer's face. Alternatively, if the movable portion 56a is not properly in contact with the wearer's face, the adjustment tool can be rotated to move the distal end portion 66a from the second position 132 to the first position 130, or from the third position 134 to either the first or second positions 130, 132, to tighten the fit.

Figure 6:
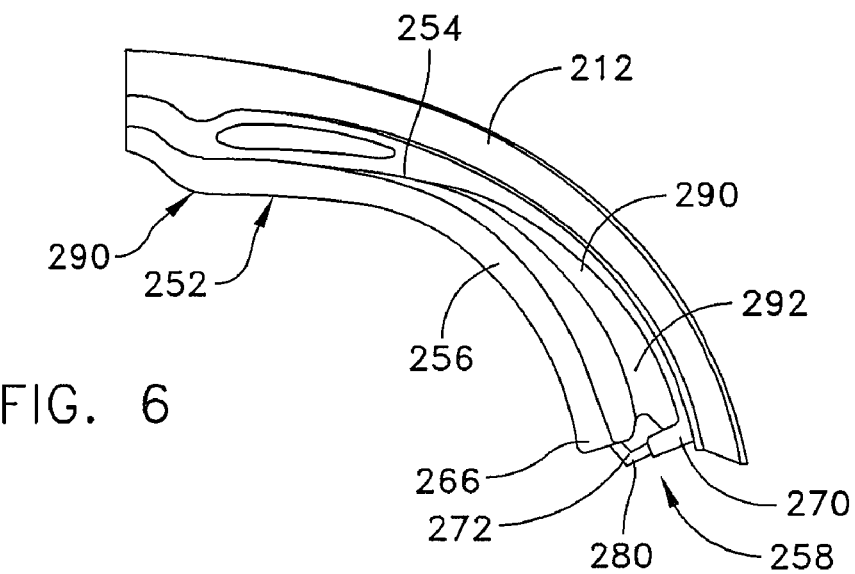
FIG. 6 is a top plan view of an eyecup according to another embodiment.

Referring to FIG. 6, another embodiment of an eyecup 240 coupled to an eyeglass frame 212 is shown. Except as otherwise noted, the eyecup 240 includes the same general features as the eyecup 40 described above. For example, the eyecup 240 includes a right side assembly 252 and a left side assembly (not shown) substantially mirroring the right side assembly. The right side assembly 252 includes a fixed portion 254 and a movable portion 256 made of a flexible material and movably coupled to the fixed portion in the same, or a similar, manner as described above in relation to the eyecup 40. Similar to the eyecup 40, the eyecup 240 is adjustable for providing a custom fit around the eyes and protecting the eyes from undesirable contaminants. However, the mechanism and method for adjusting the eyecup 240 and protecting the eyes has various differences in comparison to the eyecup 40.

A distal end portion 266 of the movable portion 256 is adjustably positioned relative to the fixed portion 254 via a detent mechanism 258. The detent mechanism 258 includes a positioner portion 270 coupled to the fixed portion 254 and a catching portion 272 coupled to the movable portion 256.

The positioner portion 270 extends generally transversely from the fixed portion 254 towards the movable portion 256 and includes a recess 274, e.g., a channel, receptacle, pocket, slot, etc., sized to receive the catching portion 272. The positioner portion 270 includes two or more linearly-aligned apertures 276 having an open end accessible from the recess 274. In the illustrated embodiments, the apertures 276 are through-apertures extending from an outer surface of the positioner portion to the recess 274. As shown, the apertures 276 are formed in an outer surface of the positioner portion 270 that faces away from the head of a user wearing the frame 212. In other implementations, the apertures 276 are formed in another surface, such as an inner surface of the positioner portion 270 that faces toward the head of a user wearing the frame 212. Although the apertures 276 are shown as through-apertures having two open ends, in some embodiments, the apertures 276 have one open end and one closed end, such as, e.g., a recess, pocket, depression, etc.

The catching portion 272 includes a base 280 extending generally transversely from the movable portion 256 towards the fixed portion 262. Attached to the base 280 is a biasing element 282, such as a leaf spring or other resiliently flexible member. The biasing element 282 includes a fixed end 284 attached to the base 280 and a free end 286 resiliently movable inwardly and outwardly relative to the base (see FIG. 8). The fixed end 284 is attached to the base 280 via any of various conventional coupling techniques, such as, for example, heat staking, bonding, adhering, mechanical fastening, etc. The biasing element 282 further includes a catch 288, such as a bump, nubbin, protrusion, or other user-engageable member, positioned proximate the free end 286. The catch 288 is sized and shaped to be received within the respective apertures 276. For example, in some implementations, the apertures 276 are circular and the catch 288 is a generally cylindrical protrusion having a circular cross-sectional shape corresponding to the circular shape of the apertures and a generally domed end. However, in other implementations, the apertures 276 and catch 288 can have any of various shapes other than circular or round, such as, for example, square, triangular, ovular, rectangular, conical, etc.

Figure 7:
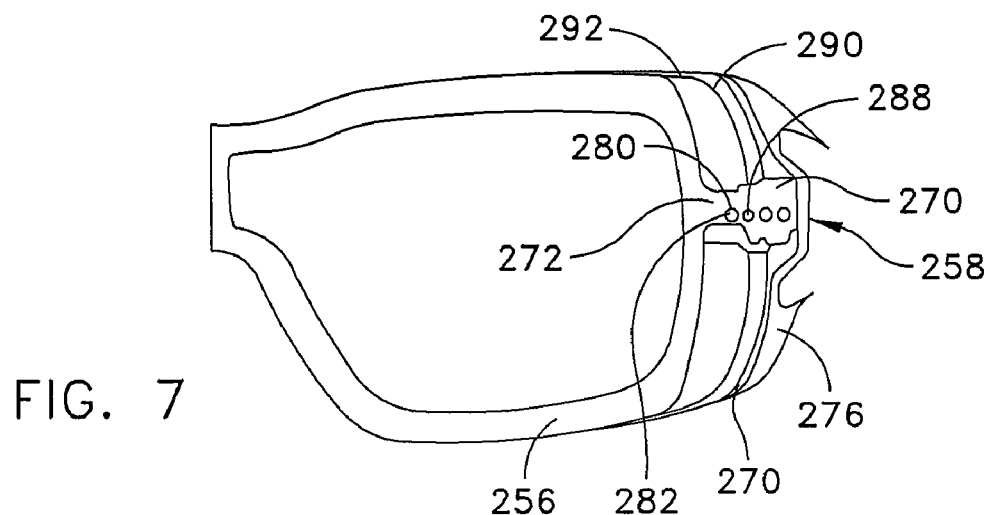
FIG. 7 is a perspective side view of the eyecup of FIG. 6.

The base 280 is positionable and movable within the recess 274. The biasing element 282 is biased in a first aperture-engaging position such that when the biasing element is aligned with one of the apertures 276, the catch 288 automatically enters and engages that aperture. With the catch 288 engaged with an aperture 276, the distal end portion 266 of the movable portion 256 is in a predetermined position relative to the fixed member 262. For example, as shown, the positioner portion 270 includes three apertures 276, e.g., a first aperture 276a, second aperture 276b, and third aperture 276c, each corresponding to a predetermined respective position of the movable portion 256 relative to the fixed portion 262. More specifically, with the catch 288 engaged with the first aperture 276a, the distal end portion 266 is retained in a first, or relatively closed, position in which the distal end portion is positioned relatively close to the fixed portion 262. With the catch 288 engaged with the second aperture 276b, the distal end portion 266 is retained in a second, or intermediate, position in which the distal end portion is positioned further away from the fixed portion 262 than when in the first position. Finally, as shown in FIGS. 6 and 7, with the catch 288 engaged with the third aperture 276c, the distal end portion 266 is retained in a third, or relatively open, position in which the distal end portion is positioned even further away from the fixed portion 262 than when in the second position.

Although the illustrated embodiments show the positioner portion 270 coupled to the fixed portion 254 and the catching portion 272 coupled to the movable portion 256, the configuration can be reversed and still achieve the advantages and features of the eyecup 240. For example, the positioner portion 270 can be coupled to the movable portion 256 and the catching portion 272 can be coupled to the fixed portion 254.

As described above in relation to the eyecup 40, the position of the movable portion 256 relative to the fixed portion 254 corresponds to the position of the movable portion relative to the face of a user wearing the frame 12. Based on various factors, such as, for example, environmental conditions, general comfort level, new user, etc., a user may desire to adjust the position of the movable portion 256 relative to his or her face. Accordingly, adjustment of the movable portion 256 is accomplished by first urging the catch 288 out of engagement with a first one of the apertures 276 and then moving the movable portion 256 toward or away from the fixed portion 254 until the catch 288 is aligned with the aperture 276 corresponding to the desired position of the distal end portion 266. The bias of the biasing element 282 urges the catch 288 into the aperture 276, such as in a snap-fit manner. The catch 288 can be urged out of engagement with an aperture 276 by applying a pressure on the catch 288 that is sufficient to overcome the biasing force of the biasing element 282. In certain implementations, pressure on the catch 288 can be applied using a readily available tool, such as the tip of a pen, pencil, or pin, finger, or other conventional or customizable instrument having a small contact area.

For convenience, in certain instances, the movable portion 256 can be adjustable in situ, i.e., while the frame 212 is being worn by the user. Also, although the illustrated eyecup 240 has three apertures 276 corresponding to three movable portion positions, in other embodiments, the eyecup can have any number of apertures 276 for increased adjustability.

The eyecup 240 also includes an eye protector 290 positioned intermediate the fixed portion 254 and movable portion 256. The eye protector 290 limits entry of contaminants through the space between the fixed and movable portions 254, 256. As shown in FIGS. 6 and 7, the eye protector 290 desirably is made of a flexible material secured to the stepped portions 263, 265 of the fixed and movable portions 254, 256, respectively (see FIG. 8). As the distal end portion 266 is moved toward or away from the fixed portion 254 during adjustment of the eyecup 240, the eye protector 290 contracts, expands, folds, unfolds, or otherwise changes in form, to provide eye protection in any of the various eyecup positions. As shown, the eye protector 290 includes a creased portion 292 that facilitates folding of the eye protector as the movable portion 256 moves toward the fixed portion 254 and unfolding of the eye protector as the movable portion moves away from the fixed portion. In certain implementations, the eye protector 290 is made from rubber or other flexible polymeric material. The eye protector 290 can be secured to the stepped portions 263, 265 via an adhesive, or other coupling technique, such as bonding, fastening, and/or molding.

Figure 8:
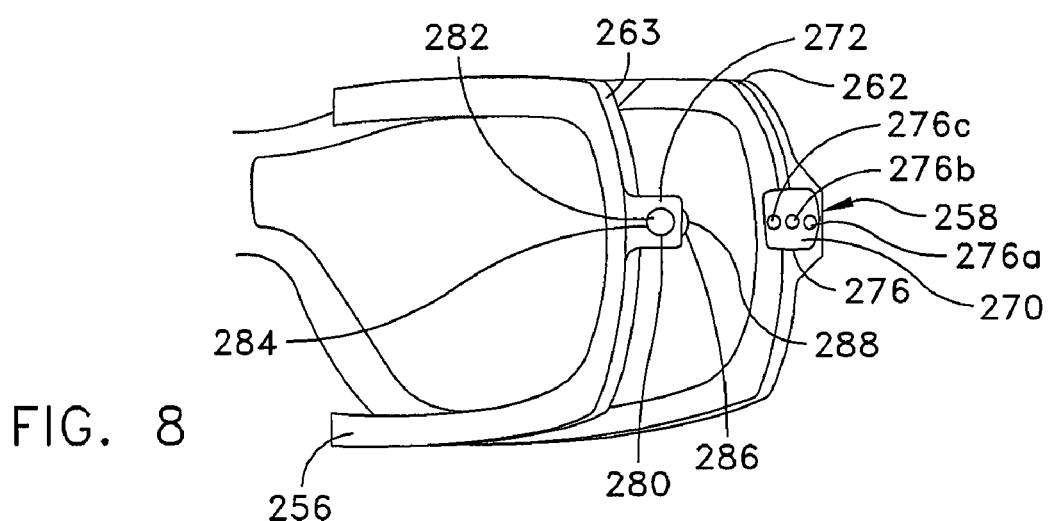
FIG. 8 is an exploded perspective side view of the eyecup of FIG. 6.

Although not shown in the embodiments of FIGS. 6-8, in some embodiments, instead of, or in addition to, a flexible material, the eye protector 290 can include a ridge, such as the ridge 62a of the eyecup 40, formed in one of the movable or fixed portions, and a recess, such as the recess 72 of the eyecup 40, formed in the other portion. Engagement between the ridge and recess can form a seal to restrict contaminants from entering the eye via the space between the fixed and movable portions 254, 252 in the same or similar manner as a flexible material.

Although not shown, in some embodiments, a resiliently conformable member can be attached to the eyecups 40, 240 to provide a more effective seal between the eyecup and the wearer's face and to promote a comfortable fit. In certain implementations, the resilient member is made of a foam cushion, while in other implementations, the resilient member is made of an elastomeric material, such as rubber or silicone.

Figure 9:
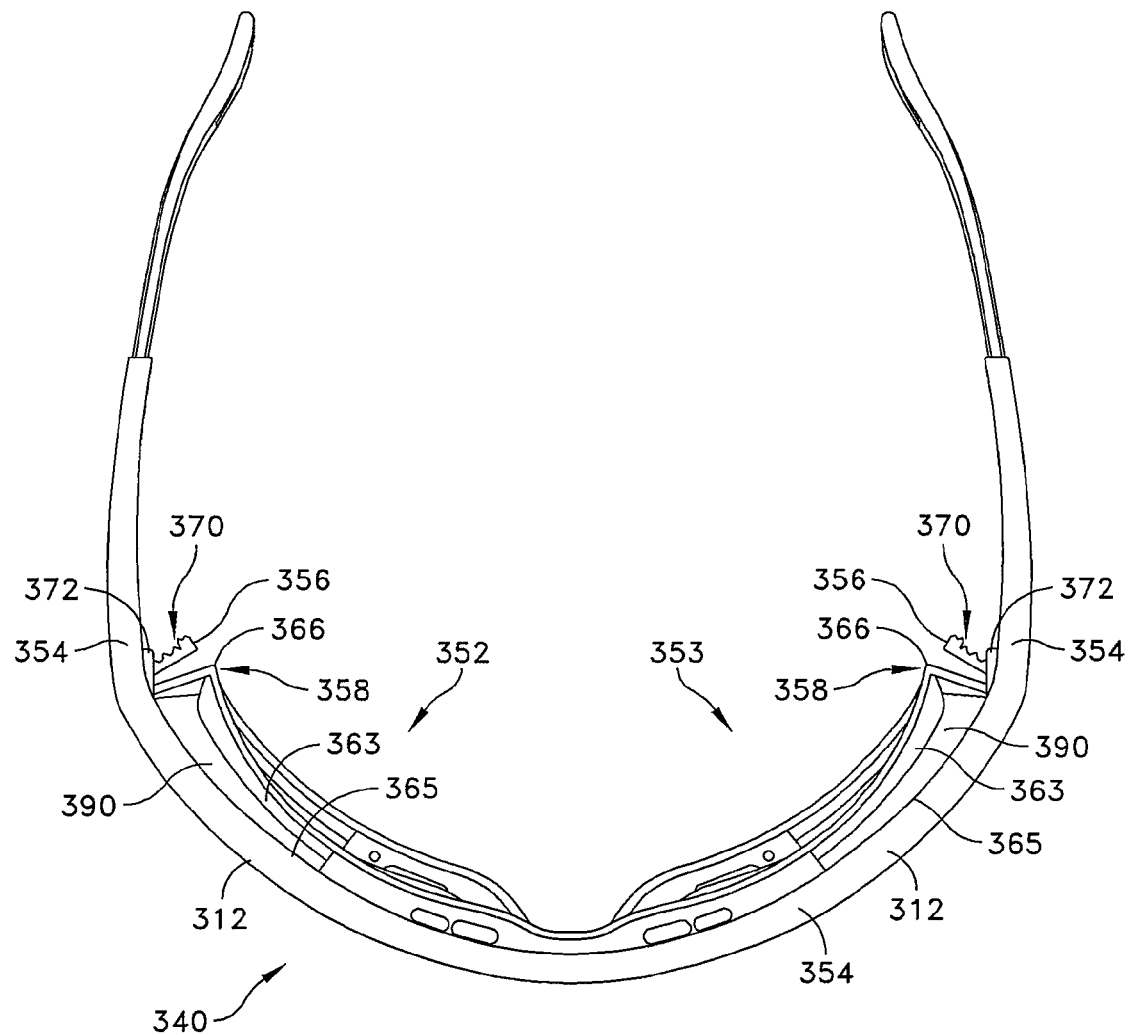
FIG. 9 is a top plan view of an eyeglass having an eyecup according to another exemplary embodiment.
Figure 10:
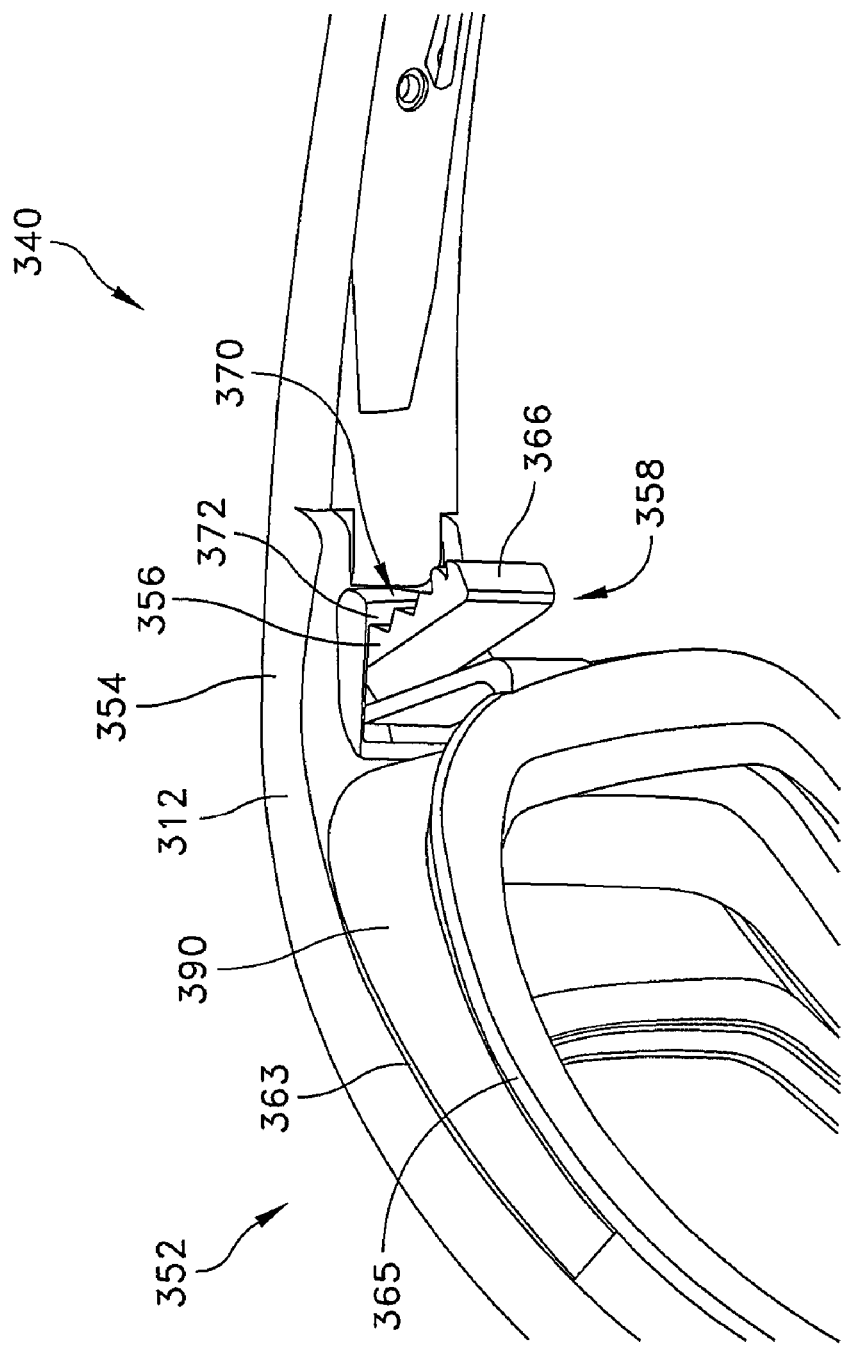
FIG. 10 is a partial view of the eyecup shown in FIG. 1.

Referring to FIGS. 9 and 10, another embodiment of an eyecup 340 coupled to an eyeglass frame 312 is shown. Except as otherwise noted, the eyecup 340 includes the same general features as the eyecup 40 described above. For example, the eyecup 340 includes a right side assembly 352 (FIG. 10) and a left side assembly 353 substantially mirroring the right side assembly 352. The right side assembly 352 includes a fixed portion 354 and a movable portion 356 made of a flexible material and movably coupled to the fixed portion in the same, or a similar, manner as described above in relation to the eyecup 40. Similar to the eyecup 40, the eyecup 340 is adjustable for providing a custom fit around the eyes and protecting the eyes from undesirable contaminants. However, the mechanism and method for adjusting the eyecup 240 and protecting the eyes has various differences in comparison to the eyecup 40.

A distal end portion 366 of the movable portion 356 is adjustably positioned relative to the fixed portion 354 via a resilient clip 358. The resilient clip 358 includes a set of teeth 370 coupled to the movable portion 356 and a flange 372 coupled to the fixed portion 354.

Although the illustrated embodiments show the resilient clip 358 with the teeth 370 coupled to the fixed portion 354 and the flange 372 coupled to the movable portion 356, the configuration can be reversed and still achieve the advantages and features of the eyecup 340. For example, the resilient clip 358 with the teeth 370 can be coupled to the movable portion 356 and the flange 372 can be coupled to the fixed portion 354.

As described above in relation to the eyecup 40, the position of the movable portion 356 relative to the fixed portion 354 corresponds to the position of the movable portion relative to the face of a user wearing the frame 12. Based on various factors, such as, for example, environmental conditions, general comfort level, new user, etc., a user may desire to adjust the position of the movable portion 356 relative to his or her face.

The eyecup 340 also includes an eye protector 390 positioned intermediate the fixed portion 354 and movable portion 356. The eye protector 390 limits entry of contaminants through the space between the fixed and movable portions 354, 356. As shown in FIGS. 9 and 10, the eye protector 390 desirably is made of a flexible material secured to the stepped portions 363, 365 of the fixed and movable portions 354, 356, respectively (see FIG. 10). As the distal end portion 366 is moved toward or away from the fixed portion 354 during adjustment of the eyecup 340, the eye protector 390 contracts, expands, folds, unfolds, or otherwise changes in form, to provide eye protection in any of the various eyecup positions. In certain implementations, the eye protector 390 is made from rubber or other flexible polymeric material. The eye protector 390 can be secured to the stepped portions 363, 365 via an adhesive, or other coupling technique, such as bonding, fastening, and/or molding.

Whereas the foregoing description is in the context of representative embodiments, the invention is not limited to those embodiments. On the contrary, the invention is intended to encompass all modifications, alternatives, and equivalents as may be included in the spirit and scope of the invention, as defined by the appended claims.

I claim:

1. An eyeglass, comprising:
a frame; and
an eyecup assembly coupled to the frame, the eyecup assembly comprising (i) a resilient side member having a first proximal portion fixed relative to the frame and a second distal portion movable relative to the frame and biased toward the frame; and (ii) an adjustment mechanism coupled to the resilient side member and positioned at least partially between the resilient side member and the frame;
wherein the adjustment mechanism comprises a detent mechanism operable to flex and un-flex the resilient side member; and
wherein the adjustment mechanism is selectively operable to flex the resilient side member to move the second distal portion away from the frame and to un-flex the resilient side member to move the second distal portion toward the frame.

2. The eyeglass of claim 1, wherein the detent mechanism comprises:
a positioner portion having a plurality of apertures; and
a catching portion movable relative to the positioner portion and having a resiliently biased catch engageable with the apertures.

3. The eyeglass of claim 1, wherein:
the eyecup assembly comprises a rigid side member mounted to the frame; and
the first proximal portion of the resilient side member is fixed to the rigid side member; and
the second distal portion of the resilient side member is movable relative to the rigid side member.

4. The eyeglass of claim 3, wherein the resilient side member is sealingly engageable with the rigid side member as the second distal portion moves away from and toward the frame.

5. The eyeglass of claim 3, wherein the second distal portion is movable into one of a plurality of predetermined positions relative to the frame.

6. The eyeglass of claim 1, wherein the eyecup assembly is a modular self-contained unit.

7. The eyeglass of claim 1, wherein the eyecup assembly extends continuously about an entire periphery of the frame.

8. An eyecup assembly for use with an eyeglass having a frame, comprising:
a body comprising at least one side portion, the body being attachable to a frame of an eyeglass such that the at least one side portion at least partially overlays an eye of a wearer when the eyeglass is worn by the wearer;
at least one side member coupled to the body and partially overlaying the at least one side portion, the at least one side member being movable relative to the at least one side portion; and
at least one adjustment mechanism positioned at least partially between a respective at least one side member and a respective at least one side portion of the body, the at least one adjustment mechanism comprising a first portion coupled to a respective one of the at least one side portion and at least one side member and a second portion coupled to the other of the at least one side portion and at least one side member;
wherein the first and second portions of the adjustment mechanism are adjustably engageable with each other to move the at least one side member into one of a plurality of predetermined positions relative to the at least one side portion.

9. The eyecup assembly of claim 8, wherein:
the at least one adjustment mechanism comprises a detent mechanism; and
the first portion is a positioner portion having a plurality of apertures and the second portion is a catching portion movable relative to the positioner portion and having a resiliently biased catch engageable with the apertures of the positioner portion.

10. The eyecup assembly of claim 8, wherein the at least one adjustment mechanism comprises a cam assembly having a cam movable relative to a cam guide to move the at least one side member relative to the at least one side portion.

11. The eyecup assembly of claim 10, wherein:
the cam guide comprises a plurality of stepped portions each corresponding to one of the plurality of predetermined positions; and
the cam guide comprises an engager separately engageable with each of the stepped portions to place the at least one side member into a respective one of the plurality of predetermined positions.

12. The eyecup assembly of claim 8, wherein the at least one side member is sealingly engageable with the at least one side portion.

13. The eyecup assembly of claim 12, wherein:
the at least one side portion comprises a projection extending adjacent a periphery of the side portion;
the at least one side member comprises a channel extending adjacent a periphery of the side member; and
the projection is at least partially positionable within the channel to form a seal between the side portion and the side member when the side member is in any of the plurality of predetermined positions.

14. The eyecup assembly of claim 8, further comprising a flexible eye protector positioned intermediate the at least one side portion and at least one side member, and wherein the at least one side member is sealingly engageable with the at least one side portion via the flexible eye protector.

15. The eyecup assembly of claim 8, wherein the plurality of predetermined positions comprises a first position in which the at least one side member is adjacent the at least one side portion, a second position in which the at least one side member is distanced away from the at least one side portion a first distance, and a third position in which the at least one side member is distanced away from the at least one side portion a second distance.

16. The eyecup assembly of claim 8, wherein:
the at least one side member is made of a resiliently flexible material; and as the at least one side member moves from one predetermined position to another predetermined position, a first portion of the at least one side member remains fixed relative to the at least one side portion and a second portion of the at least one side member is flexed about the first portion.

17. The eyecup of claim 8, wherein:
the body comprises a respective side portion for each eye of the wearer;
the at least one side member comprises a respective side member for each eye of the wearer; and
the at least one adjustment mechanism comprises a respective adjustment mechanism for each eye of the wearer.

18. A method for adjusting fit of an eyewear to a wearer, comprising:
providing an eyewear comprising a lens portion and an eyecup assembly coupled to the lens portion, the eyecup assembly comprising: (i) at least one fixed side member fixed relative to the lens portion; (ii) at least one resiliently flexible side member movably coupled to the at least one fixed side member; and (iii) at least one adjustment mechanism coupled to the at least one fixed side member and at least one resilient side member; and
adjusting the adjustment mechanism to flex the at least one resiliently flexible side member away from the at least one fixed side member or un-flex the at least one resiliently flexible side member toward the at least one fixed side member;
wherein the at least one adjustment mechanism comprises a detent mechanism having a positioning portion having a plurality of recesses coupled to a respective one of the at least one fixed side member and at least one resiliently flexible side member and a catching portion having a catch engageable with the recesses and coupled to the other of the at least one fixed side member and at least one resiliently flexible side member; and
wherein adjusting the adjustment mechanism comprises urging the catch into and out of engagement with the recesses.

19. The method of claim 18, wherein:
the at least one resiliently flexible side member is movable into a plurality of positions relative to the at least one fixed side member;
the catch is biased in a recess engaging position; and
adjusting the adjustment mechanism comprises applying a pressure to the catch sufficient to overcome the bias and move the catch out of the recess engaging position.

20. The method of claim 18, wherein:
the adjustment mechanism comprises a cam rotatably engageable with a cam guide; and
adjusting the cam mechanism comprises rotating the cam relative to the cam guide.

21. The method of claim 20, wherein:
the at least one resiliently flexible side member is movable into a plurality of positions relative to the at least one fixed side member;
the cam guide comprises a plurality of stepped portions each corresponding to one of the plurality of predetermined positions;
the cam guide comprises an engager separately engageable with each of the stepped portions; and
adjusting the adjustment mechanism comprises engaging a stepped portion of the plurality of stepped portions corresponding with a desired predetermined position with the engager to place the at least a portion of the at least one resilient side member in the desired predetermined position.

22. The method of claim 18, wherein adjusting the adjustment mechanism comprises adjusting the adjustment mechanism to bend at least a portion of the at least one resilient side member.

* * * * *